United States Patent [19]

Cukier et al.

[11] Patent Number: 4,744,882
[45] Date of Patent: May 17, 1988

[54] POLYCONDENSATES OF SULFONATED COAL TAR FRACTIONS

[75] Inventors: Samuel Cukier, Toronto; Marvin D. Camp, Jr., Mississauga, both of Canada

[73] Assignee: Domtar Inc, Montreal, Canada

[21] Appl. No.: 88

[22] Filed: Jan. 2, 1987

[51] Int. Cl.$^4$ ............................................. C10C 3/06
[52] U.S. Cl. ........................................ 208/44; 208/14; 208/22; 106/274; 106/284
[58] Field of Search ..................... 208/44, 22, 14; 106/274, 284

[56] References Cited

U.S. PATENT DOCUMENTS

| | | | |
|---|---|---|---|
| 1,353,003 | 9/1920 | White, Jr. | 106/274 |
| 2,299,469 | 10/1942 | D'Antul | 208/44 |
| 2,354,868 | 8/1944 | McKinney | 106/274 |
| 2,447,004 | 8/1948 | Gamson | 106/274 |
| 2,560,642 | 7/1951 | Greeves et al. | 208/44 |
| 3,108,060 | 10/1963 | Matthews, II | 208/44 |
| 3,130,144 | 4/1964 | Bostwick et al. | 208/44 |
| 3,152,978 | 10/1964 | Fierce et al. | 208/44 |
| 3,238,182 | 3/1966 | Goodrich | 106/274 |
| 3,275,585 | 9/1966 | Baum et al. | 208/44 |
| 3,493,404 | 2/1970 | Koons | 208/44 |
| 3,509,038 | 4/1970 | Corbett | 208/44 |
| 3,600,298 | 8/1971 | Mayumi et al. | 208/44 |
| 3,973,971 | 8/1976 | Greco et al. | 106/273 R |
| 4,024,076 | 5/1977 | Miyaki et al. | 208/44 |
| 4,260,423 | 4/1981 | Thomas | 208/44 |
| 4,559,128 | 12/1985 | Goodrich | 106/274 |

FOREIGN PATENT DOCUMENTS

| | | | |
|---|---|---|---|
| 1138801 | 1/1983 | Canada | 208/44 |
| 2155530 | 11/1970 | Fed. Rep. of Germany | 208/44 |
| 1505304 | 10/1968 | France | 106/274 |
| 1135088 | 2/1985 | Japan | 208/44 |

Primary Examiner—Helen M. S. Sneed
Assistant Examiner—Helane Myers

[57] ABSTRACT

A simpler and new process for the polycondensation of a sulfonated coal tar fraction comprising: sulfonating a coal tar fraction having a distillation range of 200° to 240° at normal pressure, with an excess of 20-30% mole of sulfuric acid, as opposed to 105% in the prior art, for 4-8 hours at a temperature of 160° C.±10° C. under reflux. The product is diluted with water to render it fluid at about 80° C. and molar ratio of formaldehyde per mole of the sulfonated coal tar fraction is then added gradually at a temperature of about 85° C.±5° C., then gradually heated for about 1 to 4 hours at 100° to 106° C., and then further raised to 106° C.–120° C. for 2 to 4 hours. The product is then cooled and neutralized. With this process, new polycondensates with improved properties are produced. The polycondensation including neutralization is completed within 16 hours from the time the formaldehyde is added.

10 Claims, No Drawings

POLYCONDENSATES OF SULFONATED COAL TAR FRACTIONS

FIELD OF THE INVENTION

This invention relates to a process for the polycondensation of sulfonated coal tar fraction and to a new product resulting therefrom.

BACKGROUND OF THE INVENTION

In general, those skilled in the art are convinced that purified naphthalene is essential to the condensation of naphthalene sulphonates: As stated in Kirk-Othmer; Encyclopedia of Chemical Technology 3rd edition Volume 15, page 715, "Approximately 5.7% of the U.S. naphthalene supply is consumed in the manufacture of tanning agents. These are derivatives of naphthalene sulfonic acids, their salts, and the sodium salts of the reaction products of the sulfonic acid and formaldehyde. Both petroleum and purified coal-tar naphthalene are used in these processes." In other words, and as is well known by those skilled in the art, in order to obtain satisfactory products, it is the general belief that purified naphthalene derived from coal-tar or petroleum have to be used which means naphthalene obtained from redistillation and/or recrystalization of the crude feed-stock.

"Naphthalene sulfonates represent another small outlet for naphthalene i.e. 1% of supply. The products are used as wetting agents and dispersants in paints and coatings and in a variety of pesticide and cleaner formulations. Their application as surfactant is expected to continue as a low growth item, although recently use of these products as concrete additive, i.e. plasticizers, may alter this pattern".

On page 720, of Kirk-Othmer as referred to above the methods of making 2-naphthalene sulfonic acids are disclosed wherein: naphthalene is reacted at a temperature above 150°, (160°) using in excess 96% $H_2SO_4$ to produce 2-naphthalene sulfonic acid (2-NSA).

In general, large excess of sulfuric acid is used such as 20-30%, and preferably 25% by weight on pure naphthalene for the sulfonation which extends over a period of 6 to 7 hours. Then polycondensation is carried out for a period of 36 hours and over at a temperature below 100° C., after further addition of concentrated sulphuric acid, thus increasing the total excess to 100-105 mole percent. The reaction product is the neutralized with calcium hydroxide and caustic soda (NaOH). The polycondensate is then filtered to remove the large amount of salt obtained by neutralization, the filtration requiring about 26 hours.

BROAD DESCRIPTION OF THE INVENTION

Applicant has now found a means to reduce the requirements for the degree of purity of reactants, the amount of reactants, and the reaction time necessary to carry out the polycondensation of a new polycondensate, which time is reduced from the order of about 36 to about 11-16 hours. Additional advantages to take into account includes the time saved in not purifying the reactants, as well as the time saved in providing means to eliminate the filtration step, thereby significantly improving the efficiency of the polycondensation process. The new products so obtained as marked advantages over those obtained in accordance with the prior art.

Broadly stated, the invention is directed to a process for the polycondensation of sulfonated coal tar fraction having a distillation range of about 200° to 240° C. at normal pressure, in the presence of about molar ratio of formaldehyde comprising; (a) sulfonating a coal tar fraction having a distillation range of about 200° to 240° C. at normal pressure and containing 85% to 95% naphthalene the remaining portion comprising other aromatic hydrocarbons with 25 to 30, and preferably about 25%, excess mole of sulfuric acid for 4-8 hours at a temperature of about 160° C.±10° C. under reflux condition to produce a sulfonated coal tar fraction; (b) cooling and diluting the reaction product obtained from step (a) with water to render the sulfonated coal tar fraction fluid at a temperature of about 80° C.; (c) adding gradually about a molar ratio of formaldehyde, per mole of the sulfonated coal tar fraction, at a temperature in the vicinity of 85° C.: say 85°±5° C.; (d) gradually raising the temperature of the sulfonated coal tar fraction containing the formaldehyde of step (c), for a period of about 1 to 4 hours at a temperature from 100° C. to 106° C., then further raising said temperature from 106° C. to 120° C. for a period of 2 to 4 hours to produce a polycondensation of the sulfonated coal fraction; (e) cooling the reaction product of step (d) and neutralizing and to resulting new products, said steps c, d and (e) being completed within 16 hours.

DESCRIPTION OF A PREFERRED EMBODIMENT

Contrary to the general belief, applicant is able to produce a condensate by reacting a coal tar fraction containing 85-95 naphthalene the remining portion being aromatic hydrocarbons with 20-30 and preferably about 25% of excess mole of sulfuric acid without further additions of sulfuric acid during the condensation stages. The presence of the coal tar components other than naphthalene does not interfere with the sulfonation, but on the contrary appears to have a synergistic effect in reducing the time for the polycondensation, and for maintaining suitable viscosity without requiring excess solvents and acids to finally yield new products.

In step (b) the addition of water is just enough to prevent solid formation, that is to maintain the fluidity. In being in the vicinity of 80 much less water is needed in order to attain this goal of minimizing water content.

In order to carry out steps (c) and (d), it is preferable to raise the temperature as much as possible under refluxing conditions without distilling the reactants.

Another aspect of the invention is that in general no purification, nor filtration of inorganic salts step is necessary because the total process is carried out without great excess of $H_2SO_4$. New polycondensates are obtained as will be seen in the Examples. In using ammonia or other products having ammonium ions also new higher polycondensate concentrates are possible.

Furthermore, in a preferred embodiment, the neutralization of the polycondensates in step (e) as referred to above, with ammonia allows for the direct making of new highly concentrated polycondensates. Although other meutralizing agents such as KOH, NaOH, Ca-(OH)$_2$ and the like may be used if desired. Such new concentrates when used in stucco are more effective than conventional products made according to the prior art, as water reducing agent in stucco slurries.

In order to carry out the invention, the reflux system used should be resistant to sulfuric acid. Amongst the most preferred neutralizing agents are KOH, NH₄OH, Ca(OH)₂ and mixtures thereof.

When NH₄OH is used, applicant is able to produce a polycondensate having at least 50% solids which is unusually high, if compared to the prior art.

In accordance with the invention, new polycondensation products are obtained by sulfonation of a coal tar fraction which could be used as dispersants and/or surfactants.

EXAMPLES

The following will serve to illustrate particular embodiments of the invention over the prior art.

EXAMPLE 1

755 g of a coal tar fraction having a distillation range of about 200°–240° C., and melting point of 75° to 78° C. was heated to about 160° C. 755 g of concentrated $H_2SO_4$ was then added to the coal tar fraction (for an excess mole of 25% of sulfuric acid) during a period of about 2-½hrs, and the sulfonation reaction is then allowed to proceed further for another 2-½ to 3-½ hours. As the mixture cooled, 272 g of water was slowly added in order to maintain the material fluid at about 80° C.

CONDENSATION PHASE

The condensation phase was as follows: At 87° C. 431 g of formalin were gradually added during a period of about 2 hours. The temperature was then gradually raised to 106° C. and held for about 1 to 1-¾ hours. The material visibly refluxed during this time. The material was then raised to 111° C. and maintained in this range for about 4-½ to 5 hours. As heating was reduced, 408 g of water were slowly added during a period of about ½ hour, to maintain fluidity at lower temperatures.

Finally, 612 g of ammonium hydroxide containing 28% $NH_3$ were added to neutralize the product during a period of about ½ hour.

The yield was 3159 g substantially 100% of the theoritical yield of a product having a non-volatile content of 50.9% of which 44.2% were organic solids and 6.7% ammonium sulfate. Thus, only 6.7/50.9 or 13% of the total solid was the ammonium sulfate component. The specific gravity at 25° C. was 1.21 and the viscosity 1140 cP. The pH of a 10% solution in $H_2O$ was 7.3, as shown in Table 1.

EXAMPLE 2

The same was repeated except that after the condensation phase a mole ratio of 4 parts of ammonia per part of potassium was used to neutralize the product. On analysis the products had the charateristics as shown on Table 1.

EXAMPLE 3

The same was repeated as in Example 1 except that the product was neutralized with equal quantities of ammonium hydroxide and KOH. The product was then analyzed and the results are shown on Table 1.

Also, the coal tar fraction was analyzed and found to contain the following:

| | |
|---|---|
| Naphthalene | 87.16% |
| 2-Methylnaphthalene | 6.26% |
| 1-Methylnaphthalene | 1.39% |
| o-, m-, and p-Cresol | 1.18% |
| Quinoline and isoquinoline | 1.00% |

TABLE 1

| | Example 1 | Example 2 | Example 3 |
|---|---|---|---|
| Cation of the sulfonate | $NH_4$ | $4NH_4/K$ | $NH_4/K$ |
| % Non-volatile material | 50.9 | 51.2 | 49.0 |
| % Sulfate | 6.7 | 7.1 | 7.8 |
| % Organic "solids" | 44.2 | 44.1 | 41.2 |
| pH at 10% concentration | 7.3 | 8.6 | 8.9 |

EXAMPLES 4, 5, 6

The products obtained from Examples 1, 2, 3 were evaluated for their ability to reduce the water demand of stucco slurries, as well as their effect on density, strength and Vicat set times were also examined. At the same time a control water reducer (Sample 2) was used as a comparison, it is sold under the Tradename "DISAL" and is manufactured from purified naphthalene according to the conventional methods. Also a control without water reducer was used (Sample 1).

The procedures were as follows: Slurry mixes were prepared as per ASTM C-305. Water, then a reducing agent from the Example or control, were poured into mixer bowl, and aged kettle stucco was then added and allowed to soak 30 seconds, then mix 30 seconds at speed no. 1.

The slurry produced was poured into a funnel to a predetermined depth while blocking the hole in the stem. At 15 seconds from the end of mixing, the slurry was allowed to flow onto a glass plate. The patty diameter was measured to determine spread. Vicat set, ASTM C-472 water reduction, density, strength, etc, were determined in the normal manner.

Test results are illustrated in Table 2.

TABLE 2

| | | RATE OF ADDITION | | WATER | | COMPRESSIVE | |
|---|---|---|---|---|---|---|---|
| | % | LBS LIQUID MSF | SPREAD CM | REDUCTION % | DENSITY LBS/CU FT | STRENGTH PSI | VICAT MIN |
| Sample 1 | 0 | 0 | 19 | 0 | 63.0 | 1200 | 23 |
| Sample 2 | 0.1 | 1.44 | 22 | 9 | 63.3 | 1225 | 23.5 |
| | 0.2 | 2.88 | 23 | 12.5 | 63.3 | 1250 | 23.0 |
| Example 1 | 0.1 | 1.44 | 22 | 12.5 | 63.4 | 1250 | 23.0 |
| | 0.2 | 2.88 | 23.5 | 17 | 63.0 | 1175 | 24.5 |
| Example 2 | 0.1 | 1.44 | 22.5 | 12.5 | 63.5 | 1100 | 25.0 |
| | 0.1 | 2.88 | 23.5 | 16 | 63.5 | 1175 | 25.0 |
| Example 3 | 0.1 | 1.44 | 22.5 | 10 | 62.9 | 1050 | 26.5 |
| | 0.2 | 2.88 | 23.5 | 14 | 62.9 | 1025 | 21.0 |

It is to be noted that with applicant's product at concentration 0.1 (as seen from examples 1,2,3) a water reduction of 12.5, 12.5 and 10 were obtained as compared to 9% with products made in accordance with the prior art. At 0.2 level 17, 16 and 14% were obtained with applicant's product as compared to 12.5% obtained with products made according to the prior art. It is also significant that the example 1 and 2 gives about the same result in water reduction as sample 2 at 0.2% level, or at double quantity.

EXAMPLE 7

This example illustrates clearly that applicant's invention cannot be used with pure naphthalene, as taught in the prior art. In accordance with the prior art, a sample of 365 g of pure naphthalene was raised to 160° C. At this temperature, over a period of about 1 hour, 367 g of $H_2SO_4$ was added. (25% moles excess) The mixture was held at about 160° C. for 5 to 6 hours. As the temperature was allowed to fall, 135 g of water was added so that the fluidity of the product could be maintained at 80° to 85° C.

CONDENSATION PHASE

For the condensation, over a 2 hour period, 242 g of formalin (37% $CH_2O$) was added. The temperature being about 70° to 90° C. Then the temperature was elevated and held in the 103°–105° C. range for 5-½ hours. The temperature was then further raised to 108° C. and held at that level for over an hour. The temperature was then allowed to fall, as the mixture cooled, 240 g of water was added over half an hour. Finally, 276 g of 28% $NH_3$ was added to neutralize the product.

The product became extremely viscous during condensation phase. The procedure had to be shortened because of serious handling difficulties due to high viscosity of the reaction product. After neutralization, it was found that the nearly gelatinous product was surrounded by a hard black residue that was between ¼ and ½ inch thick on the inside of the reactor. The more fluid product was diluted with 317 g of water and decanted. The mass of the black residue was approximately 448 g. The gelatinous product showed solids of 48.0%. After addition of water 1260 g of a product of 32.7% active solid was obtained giving a total yield of 62.7% based upon the theoretical yield as obtained in Example 1, thus showing the synergistic effect of the coal tar fraction having the distillation range of about 200° C. to 240° C.

EXAMPLE 8

Using conventional method, but a coal tar fraction in accordance with the present invention.

A coal tar fraction having a distillation range between 200°–240° C. (205.8 g) was melted and held at 128° C. To this was added 287.3 g of 96% $H_2SO_4$ over a period of 5 hours and 40 minutes. The sulfonation continued over an additional 3 hours at about 160° C. At this point the mixture was diluted with 155.8 g of water, added over 48 minutes, so that the material would remain fluid at about 80°–90° C.

THE CONDENSATION PHASE

Formalin (37% $CH_2O$) was then added (127.0 g) over the next 35 minutes at about 80° C. During the next 2 to 3 hours the mixture was raised to 110° C. and held at that temperature for about half an hour. The temperature was allowed to fall slowly over several hours during which time the addition of water was begun. The water addition continued intermittently on a fairly consistent pattern through the next 42 hours. The temperature was varied somewhat due to difficulties in maintaining fluidity under control. Small additions of formalin totalling 15.0 g were also added during this time attempting to make up for the obvious losses during the long condensation time. The condensation phase lasted a total of 47 hours.

The product was neutralized with 28% $NH_3$ by the addition of 278.6 g over a 25 minute period. The temperature rose somewhat during this procedure and a lower initial temperature and good cooling allowed the reaction at such a rate without significant loss of ammonia vapor. The product was allowed to stir while it cooled. The product had a pH at (10%) concentration of 9.0. The product was found to contain approximately 46% non-volatile matter of which about 14% was ammonium sulfate, 1211 g of a product was obtained containing 40% solid of which 28% was active and 12% ammonium sulfate giving a ratio of 28/40 or 30% inorganic salt based on total solid as compared to Example 1 having only 13% solid.

We claim:

1. A process for the polycondensation of sulfonated coal tar fraction having a distillation range of about 200° to 240° C. at normal pressure, in the presence of about molar ratio of formaldehyde, comprising:
   (a) sulfonating a coal tar fraction having a distillation range of about 200°–240° C. at normal pressure, having about 85% to 95% naphthalene the remaining portion comprising other aromatic hydrocarbons, with about 20%–30% excess mole of sulfuric acid, for about 4–8 hours at a temperature of about 160° C.±10° C. under reflux condition to produce a sulfonated coal tar fraction;
   (b) cooling and diluting the reaction product obtained from step (a) with water to render the sulfonated coal tar fraction fluid at a temperature of about 80° C.;
   (c) adding substantially a molar ratio of formaldehyde, per mole of the sulfonated coal tar fraction at a temperature of about 85° C.±5° C.;
   (d) gradually raising the temperature of the sulfonated coal tar fraction containing the formaldehyde of step (c) for a period of about 1 to 4 hours at a temperature from 100° C. to 106° C., then further raising said temperature from 106° C.–120° C. for a period of 2 to 4 hours to produce a water soluble polycondensation of the sulfonated coal fraction;
   (e) cooling the reaction product of step (d) and neutralizing, said steps c, d and (e) being completed within 16 hours.

2. The process according to claim 1 wherein in step (e), cooling the reaction product of step (d) to about 60°–70° C. and neutralizing with ammonium hydroxide.

3. The process according to claim 2 wherein the neutralization in step (e) is carried out to produce a concentrate of at least 50% solid.

4. The process according to claim 1 wherein the coal tar fraction contains about 85 to 90% naphthalene.

5. The process according to claim 1 wherein in step (e) neutralizing with potassium hydroxide.

6. The process according to claim 2 wherein in step (e) neutralizing with potassium hydroxide and ammonium hydroxide.

7. The process according to claim 1 wherein step (e) neutralizing with sodium hydroxide.

8. A polycondensated sulfonated coal tar fraction obtained from the process of claim 1.

9. The polycondensated sulfonated coal tar fraction obtained from the process of claim 1, consisting of 85 to 95% naphthalene groups, the remaining portion comprising at least one member selected from the group consisting of methylated naphthalenes and cresols, quinoline and isoquinoline.

10. The polycondensation sulfonated coal tar fraction obtained from the process of claim 2 containing about 9% by weight of ammonium ion and less than 1% sodium ion.

* * * * *